(12) United States Patent
Hachiya et al.

(10) Patent No.: US 7,642,402 B2
(45) Date of Patent: Jan. 5, 2010

(54) HUMAN PHOTOAGED SKIN MODEL

(75) Inventors: Akira Hachiya, Cincinnati, OH (US); Tsutomu Fujimura, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/311,239

(22) Filed: Dec. 20, 2005

(65) Prior Publication Data

US 2007/0143866 A1    Jun. 21, 2007

(51) Int. Cl.
*C12N 15/00* (2006.01)
*A01K 67/00* (2006.01)
*A01K 67/033* (2006.01)
*A01K 67/027* (2006.01)

(52) U.S. Cl. .................... 800/21; 800/8; 800/9; 800/18

(58) Field of Classification Search .................... 800/21, 800/8, 9; 900/18
See application file for complete search history.

(56) References Cited

U.S. PATENT DOCUMENTS 5,837,224 A * 11/1998 Voorhees et al. .............. 424/59

OTHER PUBLICATIONS

Rieben et al., Xenograft rejection: IgG1, complement and Nk cells team up to activate and destroy the endothelium. Trends Immunol. 26(1): 2-5, 2005.*
Jhappan et al., Ultraviolet radiation and cutaneous malignant melanoma. Oncogene 22(20): 3099-112, 2003.*
Del Bino et al., Ultraviolet B induces hyperproliferation and modification of epidermal differentiation in normal human skin grafted on to nude mice. Br J Dermatol. 150(4): 658-67, 2004.*
Haratake et al., UVB-induced alterations in permeability barrier function: roles for epidermal hyperproliferation and thymocyte-mediated response. J Invest Dermatol. 108(5): 769-75, 1997.*
Naganumaa et al., Delayed induction of pigmented spots on UVB-irradiated hairless mice. J Dermatol Sci. 25(1): 29-35, 2001.*
Berking et al., Photocarcinogenesis in human adult skin grafts, Carcinogenesis, 23(1):181-7, 2002.*
Inokuchi et al. Effects of fibroblasts of different origin on long term maintenance of xenotransplanted human epidermal keratinocytes in immunodeficient mice. Cell Tissue Res. 281(2): 223-9, 1995.*
Chung et al., Angiogenesis in skin aging and photoaging, J Dermatol. 34(9):593-600, 2007.*

* cited by examiner

*Primary Examiner*—Deborah Crouch
*Assistant Examiner*—Wu-Cheng Winston Shen
(74) *Attorney, Agent, or Firm*—Oblon, Spivak, McClelland, Maier & Neustadt, L.L.P.

(57) ABSTRACT

The invention provides a human photoaged skin model and an animal model which are useful for evaluating cosmetics and similar products in terms of their anti-aging or rejuvenating effect, as well as a method for producing such a skin model and such an animal model. The method of producing the human photoaged skin model is characterized in that a transplanted skin area of an immunodeficient non-human animal which has undergone transplantation of human skin is irradiated with UV-B light of 80-100 mJ/cm$^2$ for consecutive 4 to 8 weeks, and the irradiated area is left to take its own course for at least 3 weeks. A human photoaged skin model and an animal model produced through this method are also disclosed.

7 Claims, 3 Drawing Sheets

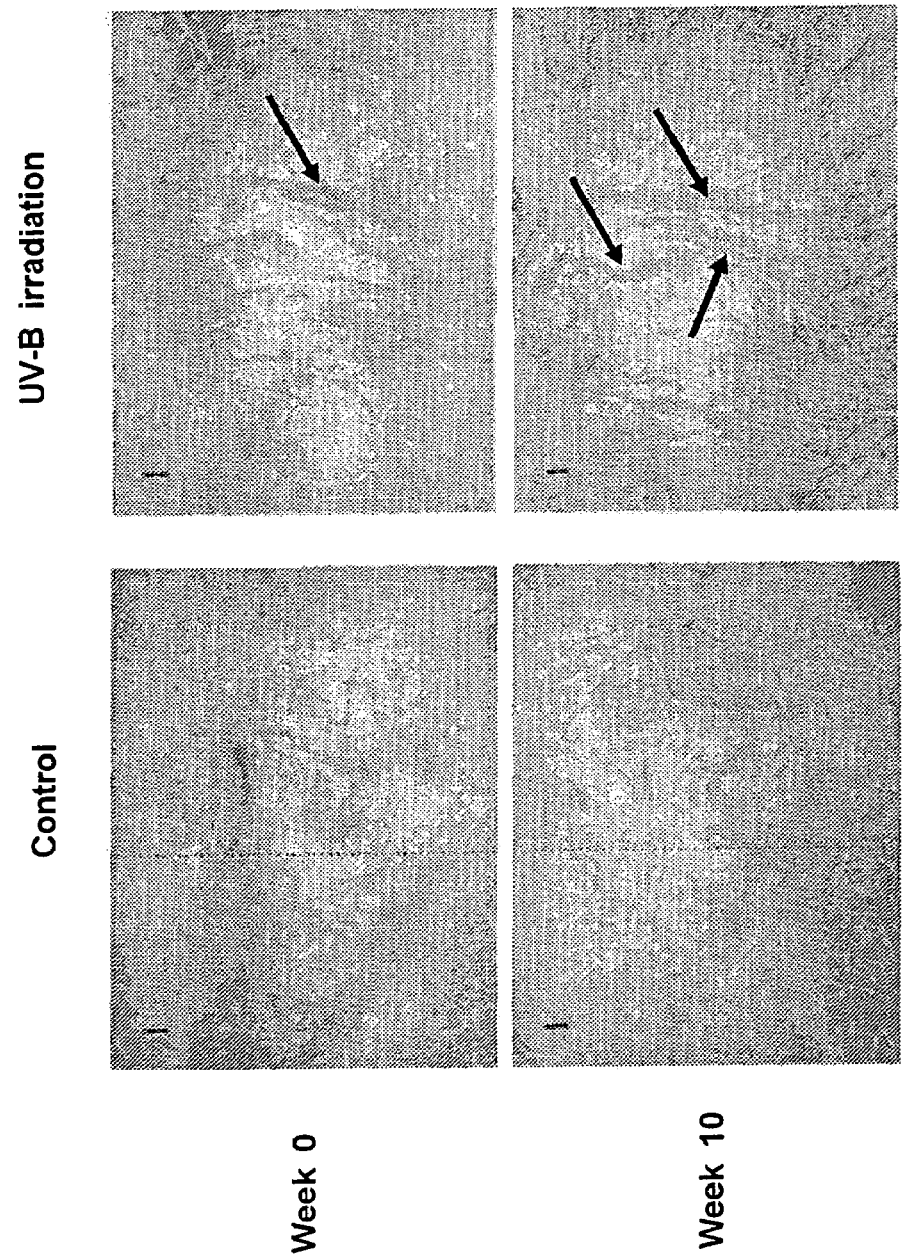

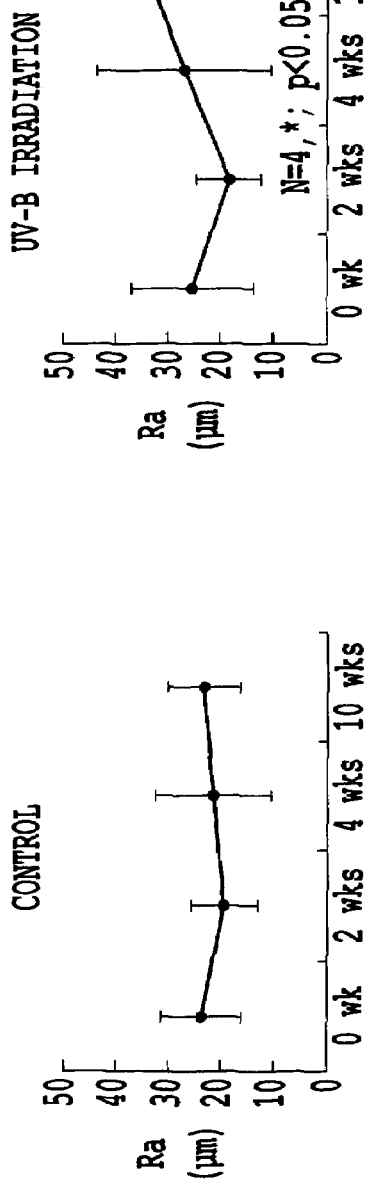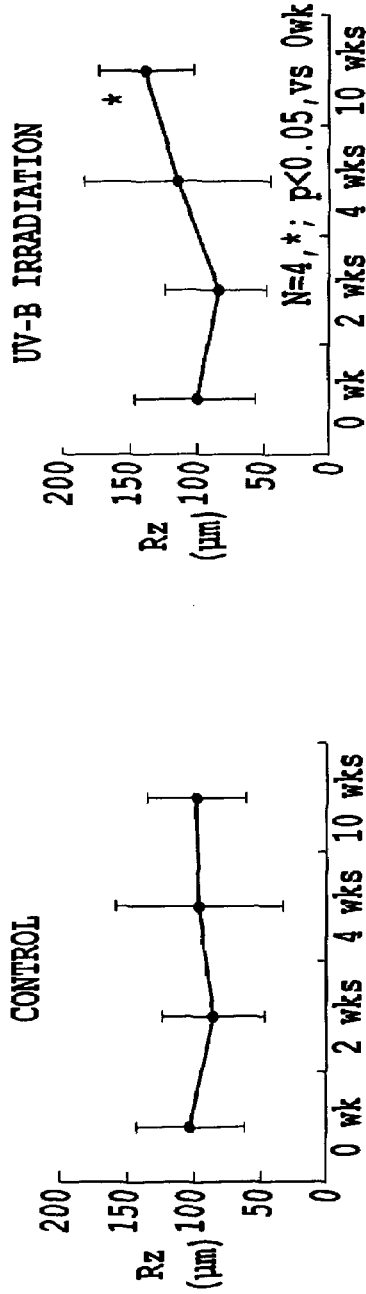

SEQUENCE LISTING

```
<160> NUMBER OF SEQ ID NOS: 1

<210> SEQ ID NO 1
<211> LENGTH: 39
<212> TYPE: DNA
<213> ORGANISM: Artificial
<220> FEATURE:
<223> OTHER INFORMATION: Synthetic DNA

<400> SEQUENCE: 1
ggccagtgaa ttgtaatacg actcactata gggaggcgg                              39
```

HUMAN PHOTOAGED SKIN MODEL

FIELD OF THE INVENTION

The present invention relates to a skin model having human photoaged skin (hereinafter referred to as a human photoaged skin model), an animal model, and a method of creating such a human photoaged skin model and such an animal model.

BACKGROUND OF THE INVENTION

As we grow older, our skin—the human skin—ages; elasticity is lost and wrinkles appear. As compared with skin areas protected from light, other skin areas that tend to be constantly exposed to sunlight, especially to ultraviolet irradiation (UV), i.e., the face, neck, and shoulders, produce significant wrinkles, sagging skin, age spots, and freckles as a result of chronic exposure to UV rays. UV rays also act to lower elasticity of the skin, increase darkening or yellowing of the skin, and reduce the moisture content of the keratinous layer. The skin aging phenomenon uniquely occurring in UV-exposed skin areas is called photoaging. In order to elucidate the photoaging mechanism of the skin and to evaluate cosmetics, pharmaceuticals, and similar products which are thought to be useful for preventing or mitigating unfavorable outcomes of photoaging; i.e., wrinkles, age spots, and freckles, a photoaged skin model would be useful if it reflects conditions of the human photoaged skin more faithfully.

For creating a photoaged skin model or an animal model, chronic exposure to UV-rays has usually been performed. Hitherto, the following exemplary methods have been known: a method in which the back skin of a hairless mouse or the paw pad skin of a rat is continuously irradiated with UV rays every day for several weeks ((1) Bissett D L, Hannon D P, and Orr T V, Photochem Photobiol. 1987; 46(3): 367-78, (2) Imayama S., Nakamura K., Takeuchi M., Hori Y., Takema Y., Sakaino Y., and Imokawa G., J. Dermatol Sci. 1994 7(1): 32-8)) and a method in which a three-dimensional model skin is irradiated in vitro with a single dose of UV light ((3) Nelson D., Gay RJ, Photochem Photobiol. 1993; 57(5): 830-7).

In relation to a model established on the basis of the human skin, there has been known a method in which a nude mouse to which human skin is transplanted is irradiated with a single dose of UV light ((4) Del Bino S., Vioux C., Rossio-Pasquier P., Jomard A., Demarchez M., Asselineau D., and Bernerd F., Br J Dermatol. 2004; 150(4): 658-67). However, in this model system, daily, continuous irradiation for several weeks is not envisaged. Accordingly, although this prior art method makes use of human-derived skin, a sufficient photoaging condition cannot be induced in the transplanted human skin, because UV irradiation is performed for only a short period of time. Thus, the model requires improvements before being recognized as a satisfactory human photoaged skin model. Presently, there has never been obtained a satisfactory human skin model or an animal model that better mimics human photoaged skin.

SUMMARY OF THE INVENTION

The present invention is directed to a method of producing a human photoaged skin model, characterized in that a transplanted skin area of an immunodeficient non-human animal which has undergone transplantation of human skin is irradiated with UV-B light of 80-100 mJ/cm² for 4 to 8 weeks consecutively, and the irradiated area is left to take its own course for at least 3 weeks.

The present invention is also directed to a human photoaged skin model produced by the above-described method.

The present invention is also directed to an animal model which bears human photoaged skin and which is produced by the above-described method.

BRIEF DESCRIPTION OF THE DRAWINGS

FIG. 1 shows comparison in terms of appearance of a transplanted skin area which had undergone 6-week irradiation with UV-B and was subsequently left for 4 weeks (i.e., at a point in time of 10 weeks).

FIG. 2a-d depicts graphs showing the results of a three-dimensional surface roughness analysis performed on replicas of the skin areas which had undergone UV-B irradiation (plotted after irradiation for 2 and 4 weeks) and 6-week UV-B irradiation with subsequent resting for 4 weeks (i.e., at a point in time of 10 weeks).

DETAILED DESCRIPTION OF THE INVENTION

Figure 3:
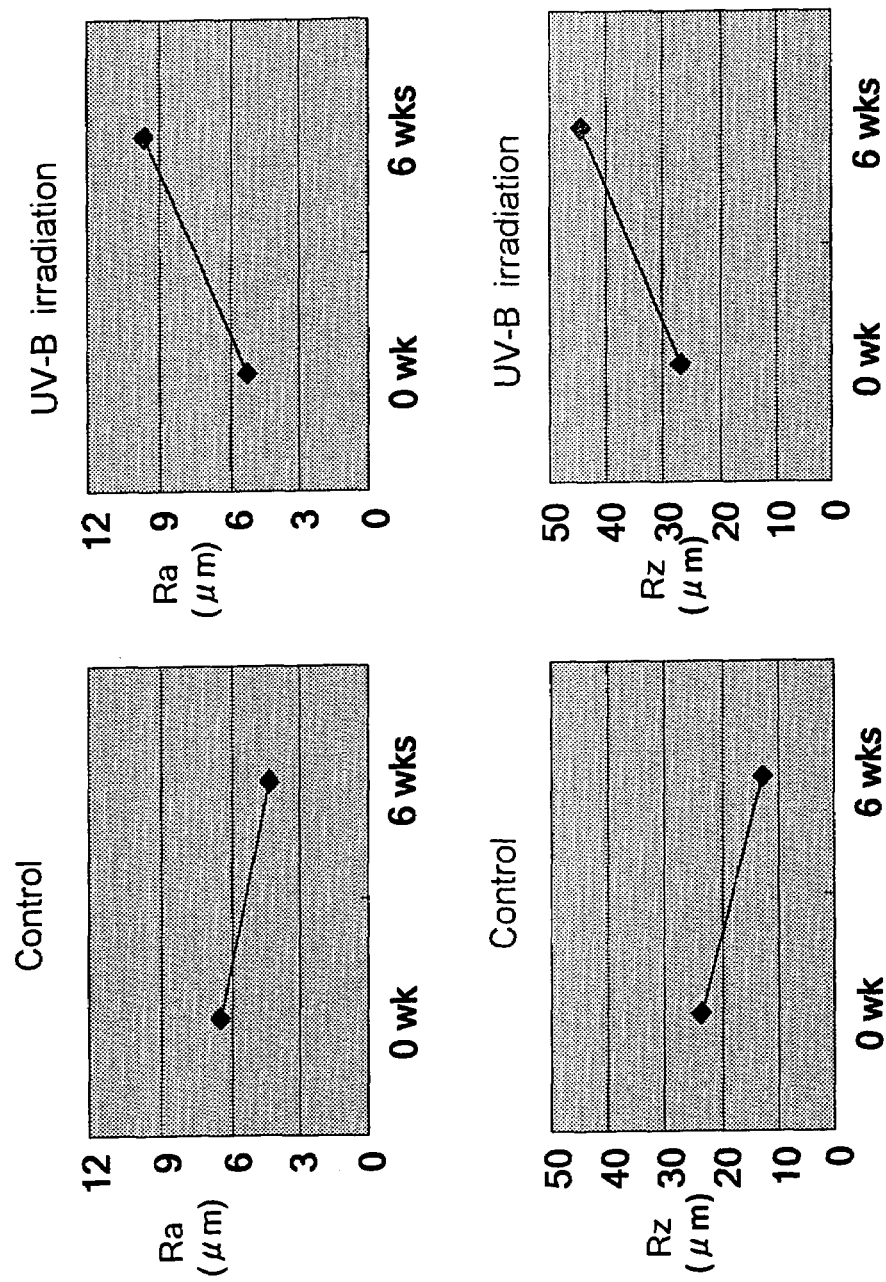
FIG. 3 depicts graphs showing the results of a three-dimensional surface roughness analysis performed on replicas of the skin areas which had undergone 6-week irradiation with UV-B light, in which abdomen-derived skin grafts were employed.

The present invention concerns provision of a skin model representing human photoaged skin (which may be referred to as a human photoaged skin model), an animal modeling human photoaging (which may be referred to as a human photoaging animal model), and a method for producing such a skin model and such an animal model. The skin model and the animal model according to the present invention are useful for evaluating the anti-aging and rejuvenating effect of cosmetics and quasi-drugs, among other products.

Through research of aging of the skin in animals to which human skin had been transplanted, the present inventors have found that when the transplanted skin area is irradiated with UV-B light of a specific dose for 4 to 8 weeks and then left as is for at least 3 weeks, there can be created an animal model bearing human "photoaged skin" which closely mimics actual human photoaging.

The method of the present invention enables, without taking a long time, provision of a human photoaged skin model or an animal model exhibiting aged skin conditions consistently, and use of such a model enables more precise elucidation of the mechanism of human skin aging and more accurate evaluation of anti-aging/rejuvenating substances.

According to the present invention, the human photoaged skin model is produced as follows: a transplanted skin area of an immunodeficient non-human animal which has undergone transplantation of human skin is irradiated with UV-B light of 80-100 mJ/cm² for 4 to 8 weeks consecutively, and the irradiated area is left to take its own course for at least 3 weeks.

As used herein, the expression "human photoaged skin model" means a certain area of skin in an animal model of human photoaged skin, the animal model bearing human photoaged skin showing the effect of aging similar to that caused by natural aging (e.g., wrinkles, saggy skin, age spots, freckles, lowered skin elasticity, increase in darkening or yellowing of the skin, and reduced water content of the keratinous layer).

In the method of the present invention, an immunodeficient animal is used as the animal. Examples of the animal include immunodeficient mice such as SCID mice, BALB cA-nu/scid, and B-17/Icr-Scid, and immunodeficient rats such as F344 Jc1-rnu. From the viewpoint of tolerance to long-term UV irradiation, use of immunodeficient mice is preferred.

These animals are preferably placed under SPF conditions, one animal per cage. The animals are commercially available from Clea Japan, Inc. or Taconic (NY).

A patch of human skin is transplanted to the above-mentioned immunodeficient non-human animal, and the patch is preferably a portion of the skin which is protected from light; e.g., the foreskin of a newborn baby or, if obtained from an adult, abdominal skin. Such a skin patch is available from circumcision or plastic surgery, or from a cadaveric skin supplied by the Skin Center.

The patch of human skin is aseptically collected so as to have a thickness of 2 to 5 mm. Until grafting to an animal, the skin patch is preferably preserved in a suitable culture medium, such as DMEM supplemented with L-glutamine and an antibiotic/antimycotic (Invitrogen, CA), under sub-confluent conditions while the temperature is maintained at 2-4° C.

Skin transplantation to an animal may be carried out in accordance with a method known in the art (Demarchez M., Hartmann D J, Herbage D., and Ville G., Dev Biol. 1987; 121 (1): 119-29). For example, the following method may be used.

Under anesthesia with isofluorane/oxygen or Nembutal, a 2×2 to 3×3 $cm^2$ wound incision is made in the dorsal skin of the animal. Before the incision was made, the skin is preferably shaved. Subsequently, a human skin graft having the same size is transplanted to the incision, and then sutured with a Nylon suture (10-20 stitches). Upon completion of suturing, analgesic treatment is preferably carried out by adding sensorcaine to the border between the skin graft and mouse skin.

Until the mice have recovered from anesthesia, they are kept in a 37° C. incubator.

Preferably, UV irradiation is started when the transplanted skin has been completely healed; i.e., about 10 weeks after transplantation.

The UV light employed is preferably UV-B light having a wavelength falling within a range of 290 to 320 nm. More preferably, the UV light has a peak in the vicinity of 302 nm.

Irradiation is preferably performed using a UV lamp held 5 to 80 cm, preferably 30 to 50 cm or thereabouts, away from the animal (specifically, the transplanted skin graft) in view of minimized uneven irradiation and ease of handling.

The UV dose is 80 to 100 $mJ/cm^2$, and irradiation is performed consecutively for 4 to 8 weeks, preferably for 6 to 8 weeks.

For avoiding any acute effect of UV rays, preferably, during the first three weeks after commencement of irradiation, the dose is increased at a rate of 10 $mJ/cm^2$ a week, and after the third week, the dose is maintained at 100 $mJ/cm^2$. That is, a preferable regimen may be as follows: 80 $mJ/cm^2$ for the first week of UV irradiation, 90 $mJ/cm^2$ for the second week, and 100 $mJ/cm^2$ for the third and subsequent weeks.

Preferably, UV irradiation is performed in such a manner that the above UV dose is irradiated once a day, 5 to 6 days per week.

After having been irradiated with UV light under the above-described conditions, the transplanted human skin graft develops aging skin conditions following a latent period of 3 weeks or more, preferably 4 weeks or more, after completion of irradiation.

Therefore, after completion of irradiation, the transplanted skin portion should be left to take its own course at least for 3 weeks, preferably 3 weeks to 6 weeks.

As shown in FIG. 1, the thus-developed aging skin conditions closely mimic photoaged skin in terms of formation of wrinkles, etc., and this state lasts for at least 8 weeks. The skin of the transplant site undergoes changes in expression of proteins which occur in photoaged skin, such as an increase or decrease in expression level of proteins including collagen I, collagen III, collagen IV, elastin (oxytalan fiber), MMP (matrix metalloproteinase) 1, MMP2, MMP13, keratin 6, keratin 12, keratin 16, filaggrin, loricrin, and involucrin.

The thus-produced human photoaged skin model and animal model of the present invention are useful for the elucidation of the mechanism of human skin aging, evaluation of anti-aging and/or aging reversing substances, and regenerative medicine.

EXAMPLES

1. Skin Grafting

A skin graft was transplanted to each of immunodeficient mice (female, 4-6 week old). Throughout the experiment period, the mice were raised under pathogen-free conditions. Immediately before transplantation of the skin graft, the dorsal hair was removed with an electric shaver, and isofluorane/oxygen (3%/0.8 liter) was used for anesthesia. During the grafting surgery, anesthetic conditions were maintained by use of isofluorane/oxygen (2%/0.7 liter). The dorsal skin of each mouse was scraped, to thereby produce a wound bed having a diameter of about 2.0-3.0 cm. A supplied skin graft; i.e., prepuce from circumcision, a patch of skin from plastic surgery, or a patch of skin from a cadaver supplied by the Skin Center, was grafted and sutured. The supplied patch of skin had been preserved in DMEM supplemented with L-glutamine and an antibiotic/antimycotic (Invitrogen, CA) until grafting (2-4° C.). After suturing, analgesic treatment was performed by adding sensorcaine to the boundary between the skin graft and mouse skin. Until recovery from the anesthetic, the mice were accommodated in a 37° C. incubator.

2. UV-B Irradiation

UV-B Irradiation was started after healing; i.e., at least 10 weeks after the transplantation surgery. A UV lamp which emits UV-B light having a peak in the vicinity of 302 nm wavelength was employed, and the distance between the lamp and the skin graft was about 30 cm.

Since MED (minimal erythema dose) of the transplanted skin was found to correspond to 50 to 80 $mJ/cm^2$, chronic irradiation of UV-B was decided to be started from a level of 80 $mJ/cm^2$. Irradiation was performed 5 days per week for 6 consecutive weeks. Before entering the third week, UV dose was increased by 10 $mJ/cm^2$ per week, and during the third to the sixth week, the dose of UV-B irradiation was maintained at 100 $mJ/cm^2$. During irradiation, the mice were allowed to freely move around in a transparent container having a floor area of 100 $cm^2$.

3. Evaluation of the Conditions of Aged Skin (1) After the start of irradiation, the surface of the transplanted skin graft was observed under a Charm View microscope (registered trademark; Moritex, Japan) using transmitted light that was reflected. In addition, digital images were captured every 2 weeks.

(2) By use of a replica agent, a replica of the transplanted skin was produced, and the replica was subjected to the following surface roughness analysis.

<Surface Roughness Analysis on Replica>

Replicas were prepared before the start of the test, and in the 2nd, 4th, and 10th weeks after the start of the test. During preparation of replicas, the animals were maintained under anesthesia with isofluorane/oxygen (2%/0.7 liter).

The skin replicas prepared by use of SILFLO (Flexico Developments) were each compressed to as flat as possible through use of another replica agent (GC exafine) with the application of pressure under a plate or similar means, and the resultant replicas were analyzed.

The three-dimensional configuration of each replica was measured by use of PRIMOS Compact (product of GF Messtechnik). After measurement, moiré fringes were eliminated through use of a filter.

A linear surface roughness analysis was performed as follows. On each of the obtained replicas, an analytical line (straight line) having a length of 7-9 mm was drawn. Along this line, linear roughness parameter values were obtained. This process was performed carefully so as not to include any shape, such as a wart, that is not considered to be caused by wrinkles. In a plane analysis, a rectangular area of about (4-5 mm)×(7-9 mm) was chosen in the central part of each of the above replicas, and within that area, the plane analysis was performed. In this case also, the area was appropriately selected so as not to include any irrelevant shape such as a wart.

The parameters employed for comparison are Ra (arithmetical mean roughness) and Rz (10-point mean roughness).

Ra: arithmetical mean roughness

Rz: 10-point mean roughness, which is a sum of the mean value of the first high to the fifth high height of monticules and the first deep to the fifth deep depth of valleys)

(3) Gene Expression Analysis with a Gene Chip

Grafted skin was harvested after 24 hours after the final irradiation. Total RNA was extracted with a Trizol reagent (Invitrogen, CA), and cleaned up using an RNeasy mini kit (Qiagen, Calif.). Purity of each RNA sample (28 s/18 s) was verified using an Aligent bioanalyzer. Biotin-labeled target cRNA was generated according to Affymetrix protocols. In short, double-stranded cDNA was generated using T7 (−dT) 24 primer 5'-GGCCAGTGAATTGTAATACGACTCACTAT AGGGAGGCGG-3' (sequence number 1) and Superscript II reverse transcriptase. cRNA from each sample was hybridized to Human Genome U133 plus 2.0 chip.

4. Results (1) Appearance

FIG. 1 shows the appearance of a grafted skin area as photographed after the relevant area was irradiated with UV-B for 6 weeks and subsequently left for 4 weeks (at a point of week 10) for comparison with a control. As is apparent from FIG. 1, the control skin did not show any significant change in skin surface configuration, whereas in the case where UV-B irradiation was performed, changes in shape including wrinkle-like linear changes, or an increase in such changes, were observed (see the arrows).

(2) Analysis of Replicas

FIG. 2 provides graphs showing, for comparison with a control, the results of a three-dimensional surface roughness analysis on replicas of grafted skin areas after the relevant areas were irradiated with UV-B, wherein the skin graft employed was foreskin and the analysis was performed 2 and 4 weeks after the start of UV-B irradiation and the analysis was also performed after 6-week UV-B irradiation with subsequent 4-week resting (i.e., at a point of week 10). As is apparent from FIG. 2, in the control case, skin showed almost no change for both roughness parameter Ra (arithmetical mean roughness) and Rz (10-point mean roughness); in other words, no change was observed in terms of roughness of the skin surface, whereas in the UV-B irradiation group, at the point in time of 10 weeks (i.e., 6 weeks of UV-B irradiation and 4 weeks of standing as being left), statistically significant increases were observed for both Ra and Rz. This result coincides with the formation of uneven skin surface; i.e., the wrinkle-like lines as shown in FIG. 1.

FIG. 3 provides graphs showing, for comparison with a control, the results of a three-dimensional surface roughness analysis on replicas of grafted skin areas after the relevant areas were irradiated with UV-B for 6 weeks, wherein the skin graft employed was abdomen-derived skin. As is apparent from FIG. 3, in the control case, skin showed almost no change for both roughness parameter Ra (arithmetical mean roughness) and Rz (10-point mean roughness); in other words, no change was observed in terms of roughness of the skin surface, whereas in the UV-B irradiation group, at the point in time of 6 weeks of irradiation, increases in both Ra and Rz were observed. This result coincides with the formation of uneven skin surface; i.e., the wrinkle-like lines as shown in FIG. 1.

(3) Gene Expression Profile

After confirmation of RNA quality, we generated the gene expression profile for UVB irradiation abdominal grafts for comparison with the non-irradiated control. The estimated changes of mRNA transcript concentration between the control and UVB groups were illustrated in log/log scatter plot. In grafted abdomen, over-expressed genes were keratin 6, keratin 16, keratin 12, MMP 13, MMP 1, involucrin, and filaggrin, and under-expressed genes were collagen I, collagen III, collagen IV, collagen VI, and MMP2.

The invention claimed is:

1. A method for producing a human photoaged skin model, comprising irradiating, with UV-B light of 80-100 mJ/cm$^2$ for 4 to 8 consecutive weeks, a transplanted skin area of an immunodeficient SCID mouse which has undergone transplantation of human skin, and allowing the irradiated skin area to develop wrinkles for a latent period of at least 3 weeks following completion of irradiation.

2. The method according to claim 1, wherein the UV-B irradiation is continually performed for 6 to 8 consecutive weeks, and afterwards, the transplanted skin area is allowed to develop aging skin conditions during a latent period of 3 to 6 weeks.

3. The method according to claim 1, wherein a UV-B irradiation dose is increased at a rate of 10 mJ/cm$^2$ a week during the first to the third weeks, and after the third week, the dose is maintained at 100 mJ/cm$^2$, such that during the first week the UV-B irradiation is at 80 mJ/cm$^2$, during the second week the irradiation is at 90 mJ/cm$^2$, and during the third week on the irradiation is at 100 mJ/cm$^2$.

4. A model for human photoaged skin produced by the method according to claim 1.

5. The method according to claim 1, wherein said SCID mouse is a BALB cA-nu/scid mouse.

6. The method according to claim 1, wherein said SCID mouse is a B-17/Icr-Scid mouse.

7. The method according to claim 2, wherein a UV-B irradiation dose is increased at a rate of 10 mJ/cm$^2$ a week during the first to the third weeks, and after the third week, the dose is maintained at 100 mJ/cm$^2$, such that during the first week the UV-B irradiation is at 80 mJ/cm$^2$, during the second week the irradiation is at 90 mJ/cm$^2$, and during the third week on the irradiation is at 100 mJ/cm$^2$.

* * * * *